United States Patent [19]
Sedlacek et al.

[11] Patent Number: 5,854,019
[45] Date of Patent: Dec. 29, 1998

[54] CELL-SPECIFIC GENE THERAPY USING AS PROMOTER NOVEL PROMOTERS FOR TISSUE INHIBITORS OF METALLOPROTEINASE-3

[75] Inventors: Hans-Harald Sedlacek, Marburg; Marisa Wick, Deutschland; Rolf Müller, Marburg, all of Germany

[73] Assignee: Hoechst Aktiengesellschaft, Frankfurt, Germany

[21] Appl. No.: 679,217

[22] Filed: Jul. 12, 1996

[30] Foreign Application Priority Data

Jul. 12, 1995 [DE] Germany ................. 195 24 720.5

[51] Int. Cl.$^6$ ........................................ C12N 1/21
[52] U.S. Cl. .............. 435/69.1; 435/69.1; 435/172.3; 435/320.1; 435/325; 435/91.4; 424/93.21; 536/23.1; 536/23.4
[58] Field of Search ............ 424/93.21; 514/44; 435/69.1, 91.4, 325, 320.1, 172.3; 536/24.1, 23.1; 935/22, 23, 33, 34, 43, 52

[56] References Cited

PUBLICATIONS

Nordeen *Luciferase Reporter Gene Vectors for Analysis of Promoters and Enhancers*, Bio Techniques vol. 6 No. 5 (1988).
Wick *Structure of the human TIMP–3 gene and its cell cycle–regulated promoter* Biochem J. 311:549–554 (1995).
Mullen, et al. *Metabolic Suicide Genes in Gene Therapy*, Pharmac. Ther. 63:199–207 (1994).
Harris, et al. *Gene therapy for cancer using tumour–specific prodrug activation*, Gene Therapy 1:170–175 (1994).
Wick, et al. *A Novel Member of Human Tissue Inhibitor of Metalloproteinases (TIMP) Gene Family Is Regulated during $G_1$ Progression, Mitogenic Stimulation, Differentiation, and Senescence* Journal biol.Chem. vol. 269 No. 29:18953–18960 (1994).
Lucibello, et al. *Sensitive Microscale Assay for the Analysis of Promoter Activity in Eukaryotic Cells*, MMCB vol. 1 No. 1:9–18 (1989).
Angel, et al. *12–O–Tetradecanoyl–Phorbol–13–Acetate Induction of the Human Collagenase Gene Is Mediated by an Indicible Enhancer Element Located in the 5′–Flanking Region*, Molec.Cell.Biol. vol. 7, No. 6:2256–2266 (1987).
Setoyama, et al. *Transcriptional activation encoded by the V–fos gene*, Proc.Natl.acad.Sci. USA 83:3213–3217 (1986).
Herber, et al. *Inducible regulatory in the human cyclin D1 promoter*, Oncogene 9:1295–1304 (1994).
Webster's II New Riverside University Dictionary, 1994, p. 67.
Clerclz et al., Gene 139, 185–191, 1994.
Apte, Genomics 19, 86–96, 1994.

Primary Examiner—Christopher S. F. Low
Assistant Examiner—Dave Trong Nguyen
Attorney, Agent, or Firm—Foley & Lardner

[57] ABSTRACT

The invention relates to promoter sequences for a gene comprising a tissue inhibitor of metalloproteinase-3 (TIMP-3). This inhibitor is found in particular in macrophages, synovial cells, and connective tissue cells. The invention also relates to cell-specific gene therapy of a subject, wherein expression of a gene in a tissue is regulated by the aforementioned promoter sequence operationally coupled to said gene. The promoter may also be used in diagnostic methods.

16 Claims, 4 Drawing Sheets

Fig. 1: Schematic representation of Exonuclease III-deletions of the 5'-flanking region of the TIMP-3 gene

Fig. 2: Nucleotide sequence of 500 bp of the human TIMP-3 promoter and 101 bp of the 5'-nontranslated region

```
-500  ATGGCTTCCC ATATCCCAGA GAGTAAGAAC CAGAGAGAGA GAGAGAAAGA GAGAGAGTTT
-440  GGGTCTTTCT CCTCTGTGCC TGCTCTCTCC AGAGAAACTG GAGGGGTAGC AGTTAGCATT
-380  CCCCCGCTGG TTCCACCAAG CACAGTCAAG GTCTCTAGGA CATGGCCACC CCTCACCTGT
-320  GGAAGCGGTC CTGCTGGGGT GGGTGGGTGT TAGTTGGTTC TGGTTTGGGT CAGAGACACC
                                 NF1
-260  CAGTGGCCCA GGTGGGCGTG GGGCCAGGGC GCAGACGAGA AGGGGCACGA GGGCTCCGCT
-200  CCGAGGACCC AGCGGCAAGC ACCGGTCCCG GGCGCGCCCC AGCCCACCCA CTCGGCGTGCC
                                                                Sp1    Sp1
-140  CACGGCGGCA TTATTCCCTA TAAGGATCTG AACGATCCGG GGGCGGCCCC GCCCCGTTAC
                          Sp1                                 C/EBP
-80   CCCTTGCCCC CGGCCCCGCC CCCTTTTTGG AGGGCCGATG AGGTAATGCG GCTCTGCCAT
                 Sp1          ↓Start
-20   TGGTCTGAGG GGGCGGGCCC CAACAGCCCG AGGCGGGGTC CCCGGGGGCC CAGGCGCTATA
+42   TCACTCGGCC GCCCAGGCAG CGGGGCAGAG CGGGGCAGCAG CAGGGCGGGCG GGCGCTCAGA
```

Fig. 3: Kinetics of induction of the $\Delta$-1010-*TIMP-3* promoter-luciferase construct after stimulation of resting NIH3T3$^{RT}$ cells by 20% FCS

Fig. 4: Analysis of transient expression of 5'-deleted TIMP-3 luciferase-constructs in normally growing, resting and serum-stimulated NIH3T3$^{RT}$ cells

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 600 base pairs
      ( B ) TYPE: nucleic acid
      ( C ) STRANDEDNESS: single
      ( D ) TOPOLOGY: linear    ( i x ) FEATURE:
      ( A ) NAME/KEY: exon
      ( B ) LOCATION: 1..540

( x i ) SEQUENCE DESCRIPTION: SEQ ID NO:1:

```
ATGGCTTCCC  ATATCCAGA  GAGTAAGAAC  CAGAGAGAGA  GAGAGAAAGA  GAGAGAGTTT      60

GGGTCTTTCT  CCTCTGTGCC  TGCTCTCTCC  AGAGAAACTG  GAGGGGTAGC  AGTTAGCATT    120

CCCCCGCTGG  TTCCACCAAG  CACAGTCAAG  GTCTCTAGGA  CATGGCCACC  CCTCACCTGT    180

GGAAGCGGTC  CTGCTGGGGT  GGGTGGGTGT  TAGTTGGTTC  TGGTTTGGGT  CAGAGACACC    240
```

-continued

| | | | | | | |
|---|---|---|---|---|---|---|
| CAGTGGCCCA | GGTGGGCGTG | GGGCCAGGGC | GCAGACGAGA | AGGGGCACGA | GGGCTCCGCT | 300 |
| CCGAGGACCC | AGCGGCAAGC | ACCGGTCCCG | GGCGCGCCCC | AGCCCACCCA | CTCGCGTGCC | 360 |
| CACGGCGGCA | TTATTCCCTA | TAAGGATCTG | AACGATCCGG | GGGCGGCCCC | GCCCGTTAC | 420 |
| CCCTTGCCCC | CGGCCCCGCC | CCCTTTTTGG | AGGGCCGATG | AGGTAATGCG | GCTCTGCCAT | 480 |
| TGGTCTGAGG | GGGCGGGCCC | CAACAGCCCG | AGGCGGGGTC | CCCGGGGGCC | CAGCGCTATA | 540 |
| TCACTCGGCC | GCCCAGGCAG | CGGGGCAGAG | CGGGCAGCAG | GCAGGCGGCG | GGCGCTCAGA | 600 |

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

| | | |
|---|---|---|
| CCGCCCGGGG | TTGTCGG | 17 |

CELL-SPECIFIC GENE THERAPY USING AS PROMOTER NOVEL PROMOTERS FOR TISSUE INHIBITORS OF METALLOPROTEINASE-3

BACKGROUND OF THE INVENTION

The invention relates to promoter sequences for the gene encoding tissue inhibitors of metalloproteinase-3 (TIMP-3). Such inhibitors are found, inter alia, in macrophages, synovial cells of the joints, ande connective tissue cells.

One of the essential problems in the in vivo administration of vectors for gene therapy is target cell-specific expression of the administered vector. An efficient method of accomplishing this is to incorporate in an expression vector a cell-specific promoter element, which element is activated by cell-specific transcription factors, thereby activating a gene sequence attached at the 3' end of the promoter (for background see reviews in Mullen, *Pharmac. Ther.* 63: 199 (1994); Harris et al., *Gene Therapy* 1: 170 (1994)). Because of the increasing use of gene therapy to cure human gene-linked diseases, there is a great need for novel cell-specific promoters.

It is an object of this invention to provide novel cell-specific promoters for gene sequences encoding tissue inhibitors of TIMP-3.

SUMMARY OF THE INVENTION

This object has been accomplished by the isolation and sequencing of a novel promoter for the tissue inhibitor of the enzyme, metalloproteinase-3 ("TIMP-3").

In another aspect of the invention, there is provided the nucleotide sequence of 500 bp of a human TIMP-3 promoter, and 101 bp of the 5'-untranslated region.

In still other aspects of the invention, there are provided uses of the promoter for regulating expression of a gene, for producing a pharmaceutical, for a diagnostic method, and for gene therapy.

DESCRIPTION OF THE FIGURES

FIG. 4 shows analyses of transient expression of the 5'-deleted TIMP-3 promotor-luciferase constructs in proliferating (FIG. 4A) and resting and serum-stimulated (FIG. 4B) NIH 3T3$^{RT}$ cells.

DETAILED DESCRIPTION OF THE PREFERRED EMBODIMENTS

There has been isolated and sequenced a novel promoter for the tissue inhibitor of the enzyme, metalloproteinase-3, which promoter is capable of cell-specific regulation of genes employed, for example, in gene therapy of subjects requiring same.

The isolation and sequencing of the promoter, as described herein, can be accomplished using laboratory procedures as described in, e.g., Sambrook et al, *Molecular Cloning, 2nd ed.*, Cold Spring Harbor Laboratory Press, Cold Spring Harbor, N.Y. 1989, which is incorporated herein by reference in its entirety.

In an initial step, the 5'-flanking promoter sequence of the human TIMP-3 gene is isolated and sequenced. Induction of TIMP-3 or mRNA expression is carried out during G0→ S progression according to Wick et al., *J. Biol. Chem.*, 269:18963 (1994), which is incorporated herein in its entirety. The 5'-flanking region of the human TIMP-3 gene is determined using the inhibitor's mRNA according to Sambrook (1989).

To sequence the promoter, an appropriate number (e.g., 1600 bp) of the 5'-flanking region of the TIMP-3 gene is deleted (from the 5'-end) by exonuclease III treatment, and cloned into a vector, preferably the Bluescript SK (−) vector. For details of the methodology, see Wick (1994) above.

Prior genomic Southern blot analyses using as a probe, for example, a radiolabeled 690 bp 5' TIMP-3 cDNA fragment, may be used to determine whether TIMP-3 represents a single or multiple gene in the human genome.

Isolation of the 5'-flanking region of the TIMP-3 gene sequence may be accomplished by hybridizing a suitable number of phages from a genomic W1-38 gene library with a 5$^1$-TIMP-3 cDNA fragment of appropriate length, e.g., about 30 bp to 300 bp. By use of restriction endonucleases together with subsequent Southern hybridization analyses, there may be determined the size of the bp fragment that contains a desired number of bp of the 5'-flanking region of the TIMP-3 gene sequence. An appropriate number (e.g., 1500 bp) of bp of the 5'-flanking region may be subjected to sequence analysis of both strands, and the transcription starting point determined.

Transcription starting points may be determined by primer extension analysis. As will be detailed in the examples below, the transcription starting point was localized to 364 bp 5' from the ATG start codon (underlined below C/EBP, third line from the bottom in FIG. 2 SEQ ID NO: 1).

Figure 1:
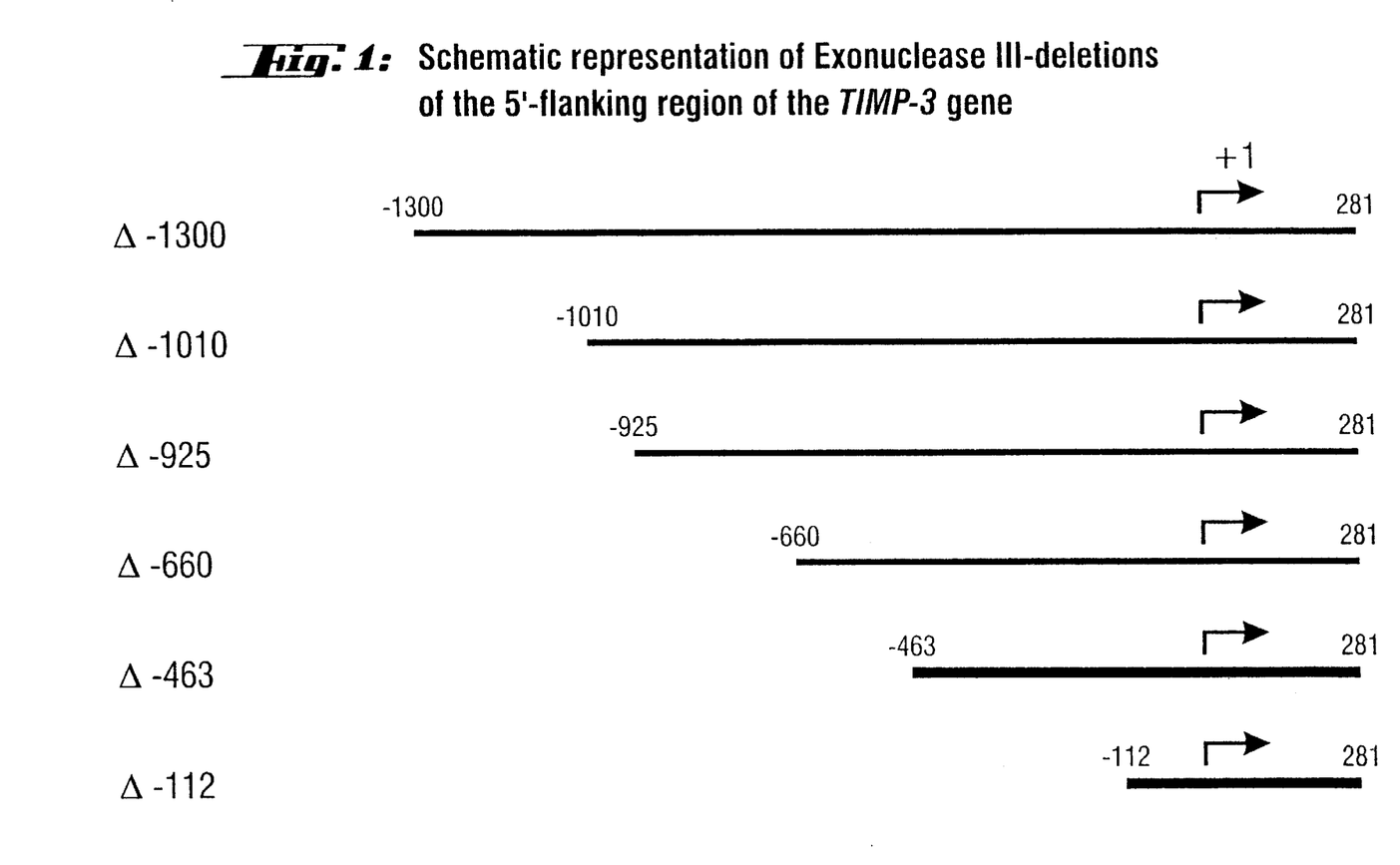
FIG. 1 shows a diagrammatic representation of the exonuclease III deletions of the 5'-flanking region of the TIMP-3 gene.

In one embodiment, the invention relates to a promoter for the gene for a tissue inhibitot of TIMP-3, comprising promoter-active DNA fragments located within position about −1010 to position about +281 as depicted in FIG. 1.

In another embodiment, the TIMP-3 promoter-active DNA fragments are located within sequence position −1010 to position +281, as depicted in FIG. 1.

Figure 2:
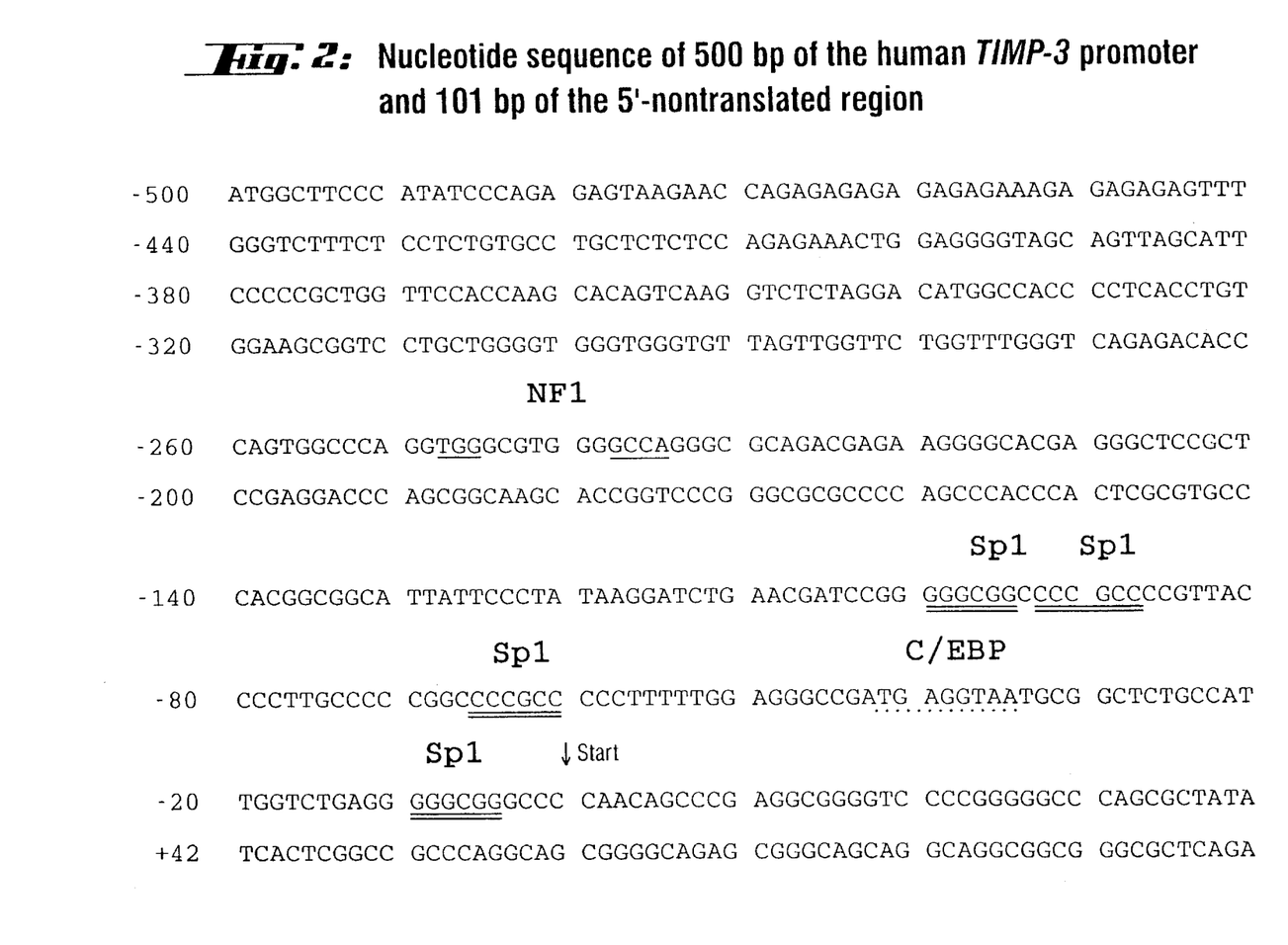
FIG. 2 shows the nucleotide sequence (SEQ ID NO: 1) of 500 bp of human TIMP-3 promoter and 101 bp of the 5'-untranslated region.

In another embodiment, the aforementioned promoter-active DNA fragments comprise a polynucleotide selected from the group consisting of sequence position about −463 to position about −10, position about −112 to position about −2, and position about −112 to position about −10, of the polynucleotide depicted in FIG. 2 SEQ ID NO: 1.

In another embodiment, the aforementioned promoter-active DNA fragments comprise a polynucleotide selected from the group consisting of positions −463 to −10, −112 to −2, and −112 to −10, of the polynucleotide depicted in FIG. 2 SEQ ID NO: 1.

The invention also relates to the polynucleotide sequence of FIG. 2 SEQ ID NO: 1 in which is located the promoter for the tissue inhibitor of TIMP-3 and 101 base pairs of the 5'-untranslated region.

The activity of the TIMP-3 promoter sequence is determined in normally proliferating, resting, and serum-stimulated cells by cloning various 5'-truncated promoter fragments upstream of the gene for a readily detectable protein, e.g., luciferase or chloramphenicol acetyl transferase enzymes. NIH 3T3 fibroblasts are particularly suitable for this purpose, although other mammalian cell lines may also be employed, such as fibroblasts and endothelial cell lines.

The activity of the TIMP-3 promoter sequence in cells may be determined with a detectable protein-TIMP-3 promoter deletion construct, and determining the extent of expression of the detectable protein gene. It may be desirable to compare the TIMP-3 promoter sequence with other known promoters (for example, see Example 4 below).

Kinetics of the induction of TIMP-3 promoter constructs after stimulation of quiescent cells may be determined as an approximation of the time point in vivo that is optimal for the expression of a desired gene.

A structure-function analyses for the isolated TIMP-3 promoter sequence and fragments thereof, which also will provide information as to the promoter regions of functional importance, may be carried out by transient expression analyses.

The promoter sequences of the invention may be employed with operationally-linked gene constructs for uses, e.g., in human gene therapy, in which direction of the gene to specific tissues, e.g., macrophages, synovial cells, or connective tissue cells, is desired. Cell-specific expression is limited only by the number of tissues in which inhibitors of TIMP-3 are found. For in vivo use, promoter-gene constructs are administered parenterally in a pharmaceutically effective vehicle (see, e.g., *Remington's Pharmaceutical Sciences,* Easton, Pa., 1990), which is incorporated herein by reference in its entirety.

The inventive promoter-gene constructs may be used in the gene treatment of rheumatism, cancer, autoimmune diseases and inflammatory processes, wherein the gene moity of the construct encodes a protein that is active against the disease in question.

Examples of genes suitable for use with the promoters of the invention are genes encoding anti-inflammatory cytokines, cytokine inhibitors, adhesion molecules, antagonists of oxygen radicals, and growth factors.

A DNA construct containing a gene operably linked to the promoters according to the present invention can be administered by aany method currently being used for gene therapy. Preferred is administration by a recombinant adenovirus vector. Such vectors can be administered at a dosage of $10^5$ to $10^8$, preferably $10^5$ to $10^6$ plaque forming units locally or intravenously.

The TIMP-3 inhibitor promoters according to the invention can be used for diagnostic procedures, for example, in rheumatoid arthritis, by well-known PCR procedures. Using suitable PCR primers, the genomic DNA of a specific cell or tissue of a patient is expanded by PCR, and the thus-produced DNA is tested for a mutated TIMP-3 inhibitor promoter, using for comparison a normal TIMP-3 inhibitor promoter.

The following is used simply to exemplify preferred embodiments, and is not to be construed as limiting the invention which is disclosed by the specification and appended claims.

EXAMPLE 1

Isolation and Sequence Analysis of the 5'-flanking Promoter Sequence of the Human TIMP-3 Gene Induction of TIMP-3 mRNA expression during G0→ S progression is based mainly on activation of the transcription of the TIMP-3 gene according to Wick (1994) above.

The 5'-flanking sequence of the human TIMP-3 gene was cloned, the starting point for the transcription of the TIMP-3 mRNA was determined, and the adjacent promoter region was subjected to a structure/function analysis. These experiments clarify the mechanisms of regulation, which form the basis of the specific TIMP-3-expression during the G0→ S and G1→ S progression.

To facilitate sequencing, almost 1600 bp of the 5'-flanking TIMP-3 gene region were deleted, starting from the 5' end, by treatment with exonuclease III and cloned into the Bluescript SK (–) vector. The names of the plasmids designate their 5'-truncation size (for example, Δ-1300 contains 1300 bp 5' from the transcription starting point). The transcription starting point is marked with +1 (see FIG. 1 and compare with FIG. 2).

Prior genomic Southern blot analyses were used to determine whether TIMP-3 represents a single gene in the human genome or whether there exist several loci for the TIMP-3 gene or, possibly, also TIMP-3 pseudogenes. For this purpose, genomic DNA was isolated from WI-38 cells, treated with the restriction endonucleases EcoRI, PstI and HindIII and subjected to a Southern blot analysis. The radiolabeled probe used was a 5'-TIMP-3 cDNA fragment with a length of 690 bp [**INSERT: origin}. As the probe recognized only one specific DNA fragment in all cases, it can be assumed that there is only one unique TIMP-3 gene present in the human genome.

To isolate the 5'-flanking region of the TIMP-3 gene, about $7 \times 10^5$ phages from a genomic WI-38 gene library were hybridized with a 5'-TIMP-3 CDNA fragment with a length of 300 bp from Wick et al. 1995 above. Of the thirteen recombinant phage clones isolated after this initial investigation, four were also recognized by an oligonucleotide with a length of 30 bp from the 5' end region of the TIMP-3 cDNA. As these phages probably also contained the 5' sequence region flanking the ATG start codon, one of the phage clones was selected for detailed characterization and analysis.

It was determined by combined treatment with various restriction endonucleases and subsequent Southern blot analysis that the genomic DNA insert with a length of 13 kb in this phage contained about 4.7 kb of the 5'-flanking TIMP-3 gene sequence. The nucleotide sequence of approximately 1500 bp of the 5'-flanking gene region was determined by sequence analysis of the two strands. The 5' deletions (truncations) of the cloned 5' gene region prepared for this purpose by exonuclease III treatment are illustrated in FIG. 1.

The sequence region which emerged from the structure/function analyses (see below) as particularly important for the TIMP-3 promoter function is shown in FIG. 2. Computer-assisted analysis was used to identify in the TIMP-3 promoter sequence a number of elements which resemble the binding sites of known transcription factors. These elements include, inter alia, 4 Spl binding sites, a possible NF1 site, and a C/EBP binding site (marked in FIG. 2). GC boxes (Spl binding sites, double underlined), two half sides of a possible NF1 binding site, and an element resembling the C/EBP binding site (dotted underline) are marked. The transcription starting point is indicated by an arrow.

EXAMPLE 2

Mapping of the Transcription Starting Point of the TIMP-3 MRNA

In order to establish the starting point(s) for initiation of transcription, the 5' end of the TIMP-3 mRNA was determined by primer extension analysis. This identified a transcription starting point (nucleotide sequence SEQ ID NO: 2: CCGCCCGGGGTTGTCGG) which is located 364 bp 5' from the ATG start codon (marked in FIG. 2). Despite detailed investigation of the nucleotide sequence located upstream of the starting point, neither a TATA box nor TATA-like sequences were found.

EXAMPLE 3

Activity of the TIMP-3 Promoter Sequence

In order to determine the activity of the TIMP-3 promoter sequence in normally proliferating, resting and serum-stimulated cells and to obtain initial indications of functionally important promoter regions, the 5'-deleted promoter fragments used for the sequencing (see FIG. 1) were cloned upstream of the luciferase gene into the promoterless pXP-2 vector according to Nordeen, *Biotechniques* 6, 454 (1988) which is incorporated herein by reference in its entirety. Owing to its extremely low baseline activity, this reporter construct is particularly suitable for carrying out transient expression analyses.

EXAMPLE 4

Activity of the TIMP-3 Promoter Sequence in Normally Proliferating and Serum-Stimulated NIH 3T3 Cells In order to show that the isolated TIMP-3 promoter sequence is active in transient expression analyses, i.e. can control the transcription of the luciferase reporter gene, the TIMP-3 promoter deletion construct −1010 (comprises nucleotides −1010 to +281, see FIG. 1) was transfected into NIH 3T3 cells, and the luciferase activity in these normally proliferating or serum-stimulated transfected cells was determined. For comparison, expression was additionally measured for other luciferase-promoter constructs which containe d the herpes virus tk promoter (pT81; Lucibello et al., *Meth. Mol. Cell Biol.* 1: 9 (1989)), a 5xTRE minimal promoter (Angel et al., *Mol. Cell Biol.* 7: 2256 (1987)), an RSV-LTR (Setoyama et al., *Proc. Natl. Acad. Sci. USA* 83: 3213 (1986)) or a fragment with a length of 937 bp of the human cyclin D1 promoter (Herber et al., *Oncogene* 9: 1295 (1994)). All references are incorporated herein by reference. The results of these investigations are listed in Table 1.

Expression of various promoter-luciferase constructs was determined in normally proliferating (Table 1A) and serum-stimulated (Table 1B) NIH 3T3 cells. After DEAE transfection of 7 μg of plasmid DNA, the NIH 3T3 cells were incubated in serum-containing (A) or serum-free (B) medium for 40 h and stimulated with 20% fetal calf serum for 4 h (B), and the expression of the luciferase reporter gene determined.

TABLE 1

| A. Expression in proliferating cells (RLU × 10³) | |
| --- | --- |
| TIMP-3 Δ −1010 | 189.5 ± 6.4 |
| pRSV-LTR | 308.1 ± 23.4 |
| p5 × TRE | 59.1 ± 2.2 |
| Cyclin D1 Δ −973 | 27.8 ± 3.5 |
| pXP2 | 0.2 |

| B. Relative induction by 20% FCS in FCS-stimulated versus | |
| --- | --- |
| G0 cells | (Factor) |
| TIMP-3 Δ −1010 | 8.4 ± 0.4 |
| p5 × TRE | 2.4 ± 0.2 |
| Cyclin D1 Δ −973 | 3.5 ± 0.3 |
| pT81 | 1.0 ± 0.2 |
| pXP2 | 1.2 |

Expression of the TIMP-3 promoter construct Δ-1010 in normally proliferating NIH 3T3 cells (Table 1 A) was about 3 times higher than the 5xTRE minimal promoter and 7 times higher than the cyclin D1 promoter construct. Only the RSV-LTR reporter plasmid showed a higher activity, about 2-fold higher than the TIMP-3 promoter construct. These results indicate that the human TIMP-3 promoter has comparatively high transcriptional activity, as shown in Table 1B and FIG. 3.

After DEAE transfection of 7 μg of plasmid DNA, the NIH 3T3$^{RT}$ cells were incubated in serum-free medium for 40 h and stimulated with 20% FCS, and expression of the luciferase reporter gene was determined at the stated times, the data show that the TIMP-3 promoter construct Δ-1010 was also distinctly induced in cells which had been stimulated with 20% FCS for 4 h after being deprived of serum for 2 days. Compared with resting cells, the expression in this case rose by about 7- to 8- folds, which was about 3.5-fold and 2.4-fold, respectively, higher than the induction observed with the 5xTRE reporter construct and the cyclin D1 promoter construct. By contrast, the herpes simplex tk promoter-luciferase construct (pT81) showed no induction of its expression after serum stimulation.

Figure 3:
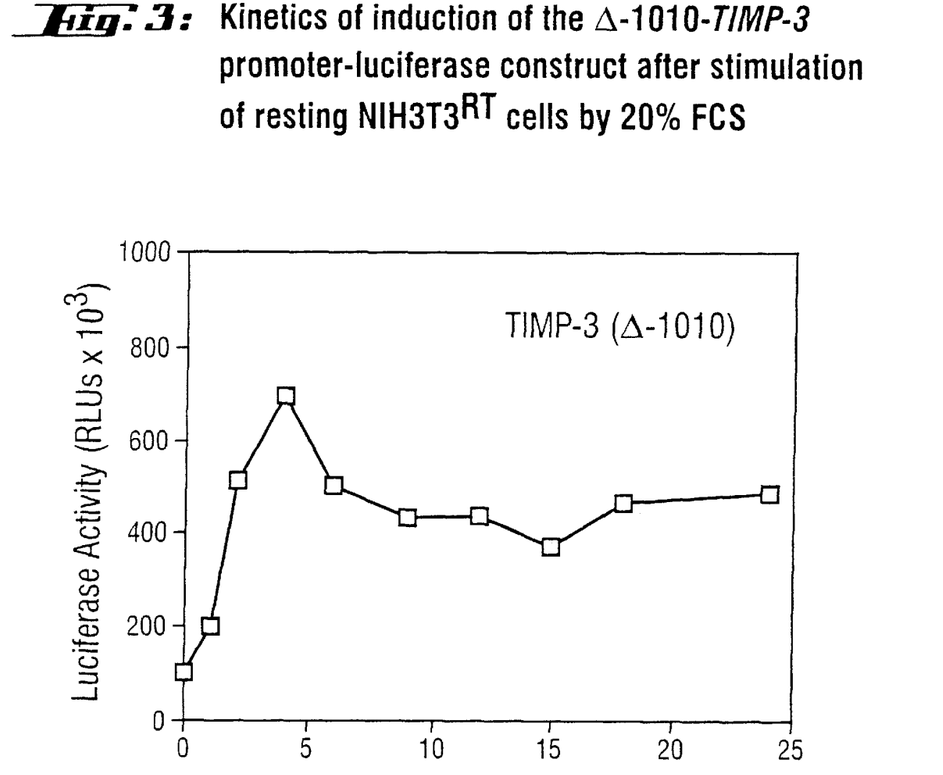
FIG. 3 shows induction kinetics for the Δ-1010-TIMP-3 promoter-luciferase construct after stimulation of resting NIH 3T3$^{RT}$ cells with 20% fetal calf serum.

FIG. 3 shows the kinetics of induction of the Δ-1010 TIMP-3 promoter construct after serum stimulation of resting cells. The luciferase activity showed a rise after only 1 h and reached maximal values, with a 7-fold induction, after 4 h.

In summary, the results demonstrate that the Δ-1010 TIMP-3 promoter construct used has the essential regulatory elements necessary for efficient transcription and for inducibility by serum.

EXAMPLE 5

Structure and Function Analysis of the TIMP-3 Promoter Sequence

Figures 4, 4A:
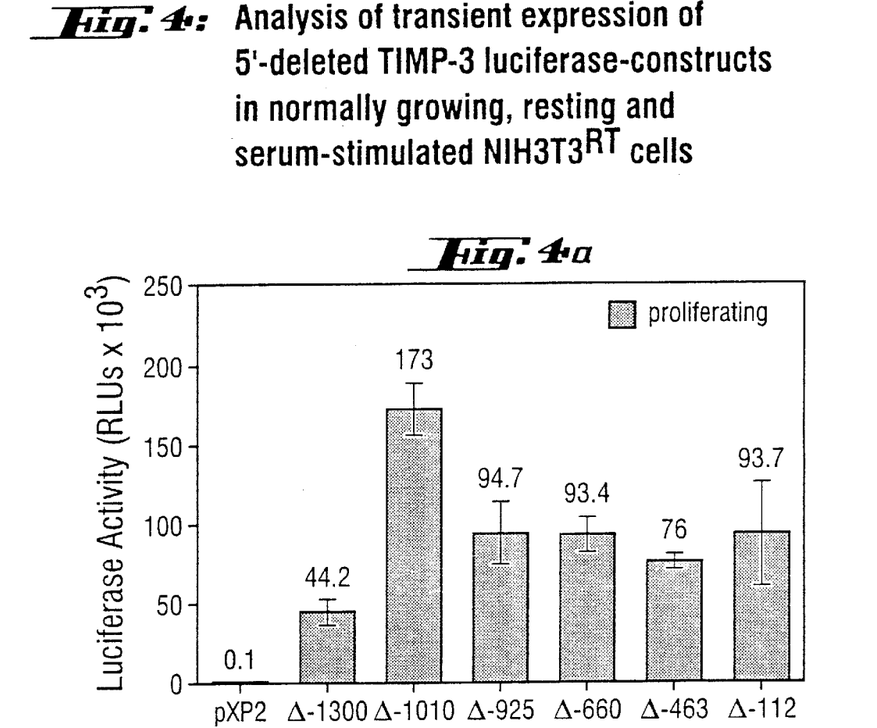

A structure and function analysis of the isolated TIMP-3 promoter sequence was carried out to provide initial indications of the promoter regions of functional importance for baseline expression and for serum inducibility. For this purpose, the activity of the various TIMP-3 promoter deletion constructs (see FIG. 1) which had been prepared for promoter sequencing and recloned into the pXP-2 vector, was determined in transient expression analyses. Analysis of the baseline expression of the various deletion constructs in normally proliferating NIH 3T3 cells is shown in FIG. 4. In this figure the plasmids have been designated according to their truncations (see FIG. 1).

(4a) Analysis in normally proliferating NIH 3T3 cells.

Figure 4B:
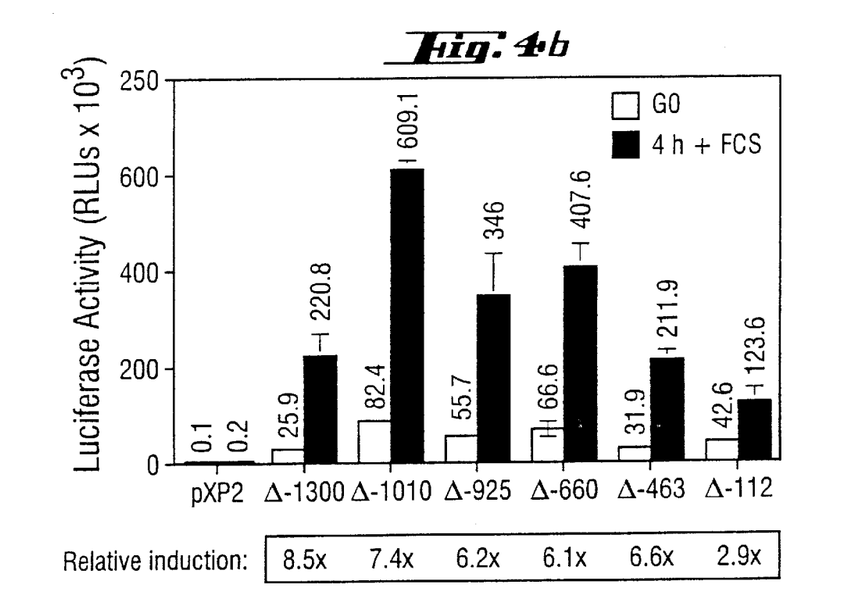

(4b) Analysis of the same constructs as in (4a) in resting cells compared with NIH 3T3 cells stimulated with 20% FCS for 4 h.

The analyses in (a) and (b) were carried out in triplicate as described in Table 1 with plasmid DNAs prepared independently of one another. Standard deviations are depicted as bars. Absence of the bars indicates a very low standard deviation which cannot be depicted in the graph.

The data yielded three main results:

1. The strongest expression was shown by the promoter construct Δ-1010. Truncation by a further 85 bp (construct Δ-925) led to a fall by almost 2-fold in the promoter activity. This indicates the presence of one or more elements involved in the transcription activation in the region between position −1010 and −925.

2. Further truncations of the 5' end as far as position −112 had no significant effect on the promoter activity. The region between −925 and −112 therefore probably contains no sequence regions important for promoter activity.

3. The region between position −1300 and −1010 appears, by contrast, to exert an adverse effect on promoter activity, which is expressed by the approximately 4-fold reduction in the expression of the Δ-1300 deletion construct compared with the promoter construct Δ-1010.

In the concluding experiment, the serum-inducibility of the various TIMP-3 promoter deletion constructs was analyzed. The results of these expression analyses, which were carried out as described in Table 1, are depicted in FIG. 4b. There is a noticeable similarity in expression profile between normally proliferating (FIG. 4a), resting and serum-stimulated cells (FIG. 4b). However, the expression levels in resting cells were less than half those in proliferating cells and were induced 2.9 to 8.5-fold 4 h after serum stimulation. As shown in the proliferating cells (FIG. 4a), the region between position Δ-1300 and Δ-1010 exerts an adverse effect on promoter activity in resting and serum-stimulated cells, but has no effect on the serum inducibility of the construct Δ-1300 (8.5-fold induction). In this case too, the highest luciferase activities were again found with the deletion construct −1010. Further truncations of the 5' end as far as position −660 led only to a fall of 1.5 to 2-fold in the promoter activity. All these constructs (Δ-1300, Δ-1010, Δ-925, Δ-660) showed, however, a distinct 6- to 8-fold induction after serum addition. Truncation by a further 200 bp as far as position −463 (Δ-463) brought about a further 2-fold fall in activity, but likewise had no effect on the serum inducibility of the construct. Only the construct Δ-112 showed a 50–65% reduction in its serum inducibility with an only 3-fold increase in expression after serum stimulation. This indicates that the region between position −463 and −112 contains element(s) important for the serum inducibility of the TIMP-3 promoter. Additional regions between position −463 and −660, and −925 and −1010, increase the serum-induced promoter activity in a general and cell cycle-independent manner.

SUMMARY OF RESULTS

The results of the characterization and the structure and function analyses of the 5'-flanking TIMP-3 gene region can be summarized as follows:

TIMP-3 is a TATΔ-boxless gene. However, transcription is nevertheless initiated at only one starting point 364 bp upstream of the ATG start codon. Compared with other promoters, the TIMP-3 promoter sequence has a relatively high activity, for which the first 112 bp are sufficient. Numerous Sp1 binding sites are located in this region. In addition, it shows distinct induction of its activity after serum stimulation of resting cells, whose kinetics correspond to TIMP-3 mRNA expression during the G0→ S progression. The regulatory elements responsible for the serum inducibility are located in the region between position −112 and −463 SEQ ID NO: 1).

Incorporated herein by reference in its entirety, including specification, claims and abstract, is priority document: Federal Republic of Germany, application no. 19524720.5, filed Jul. 12, 1995.

What is claimed is:

1. An isolated promoter for the gene of a tissue inhibitor of metalloproteinase-3, comprising promoter-active DNA fragments located in the 5'-flanking region of the human TIMP-3 gene and which are sufficient for transcriptional control of said TIMP-3 gene.

2. An isolated promoter for the gene of a tissue inhibitor of metalloproteinase-3, comprising promoter-active DNA fragments located within nucleotide position −500 to position +101, of the polynucleotide depicted in FIG. 2 (SEQ ID NO: 1).

3. An isolated promoter according to claim 2, wherein said nucleotide sequence is selected from the group consisting of position about −463 to position −10, position −112 to position −2, and position −112 to −10SEQ ID NO: 1.

4. An isolated promoter to claim 1, wherein said promoter-active DNA fragments are located within nucleotide position −1010 to position +281, relative to the transcriptional start site of said TIMP-3 gene.

5. An isolated promoter according to claim 2, wherein the promoter-active DNA fragments are located within nucleotide position −500 to position +101SEQ ID NO: 1.

6. An isolated promoter sequence according to claim 3, wherein said sequence is selected from the group consisting of position −463 to position −10, position −112 to position −2, and position −112 to position −10.

7. A composition, comprising a gene operationally coupled to a promoter and an acceptable carrier, wherein said promoter comprises promoter-active DNA fragments that are located in the 5'-flanking region of the human TIMP-3 gene and are sufficient for transcriptional control of said TIMP-3 gene.

8. A composition according to claim 7, wherein said promoter-active DNA fragments comprise DNA fragments located within nucleotide position −500 to position +101, of the polynucleotide depicted in FIG. 2 (SEQ ID NO. 1).

9. A composition according to claim 8, wherein said promoter-active fragments comprise a nucleotide sequence selected from the group consisting of nucleotide position −463 to position −10, position −112 to position −2, and position −112 to position −10 of SEQ ID NO. 1.

10. A composition of claim 7, wherein said gene is required in the treatment or diagnosis of a disease in a subject.

11. A composition of claim 8, wherein said gene is required in the treatment or diagnosis of a disease in a subject.

12. A composition of claim 9, wherein said gene is required in the treatment or diagnosis of a disease in a subject.

13. A method for regulating the expression of a gene in vitro, comprising:
    (a) providing said gene operationally coupled to a tissue human TIMP-3 inhibitor promoter;
    (b) transferring said operationally coupled gene to a cell in vitro; and
    (c) expressing said genes wherein said expression is increased in the presence of serum in the culture medium.

14. A method for regulating the expression of a gene in vitro according to claim 13, comprising:
    (a) providing said gene operationally coupled to a tissue promoter, which comprises promoter-active DNA fragments located in the 5'-flanking region of the human TIMP-3 gene and which are sufficient for transcriptional control of said TIMP-3 gene;
    (b) transferring said operationally coupled gene to a cell in vitro; and
    (c) expressing said gene,
wherein said expression is increased in the presence of serum in the culture medium.

15. A method for regulating the expression of a gene in vitro according to claim 14, comprising:
    (a) providing said gene operationally coupled to a tissue promoter, which comprises promoter-active DNA fragments located within nucleotide position −500 to position +101, of the polynucleotide depicted in FIG. 2 (SEQ ID NO. 1);
    (b) transferring said operationally coupled gene to a cell in vitro; and
    (c) expressing said gene,
wherein said expression is increased in the presence of serum in the culture medium.

16. A method for regulating the expression of a gene in vitro according to claim 15, comprising:
    (a) providing said gene operationally coupled to a tissue promoter, comprising a nucleotide sequence selected from the group consisting of position −463 to position −10, position −112 to position −2, and position −112 to position −10 of SEQ ID NO. 1;

(b) transferring said operationally coupled gene to a cell in vitro; and (c) expressing said gene, wherein said expression is increased in the presence of serum in the culture medium.

* * * * *